US012667538B2

(12) United States Patent
Chen et al.

(10) Patent No.: US 12,667,538 B2
(45) Date of Patent: Jun. 30, 2026

(54) VILAZODONE PHARMACEUTICAL COMPOSITION, PREPARATION METHOD THEREFOR AND USE THEREOF

(71) Applicant: SHANGHAI YONSUN BIOTECHNOLOGY CO., LTD., Shanghai (CN)

(72) Inventors: Zhixiang Chen, Shanghai (CN); Bao Sun, Shanghai (CN); Tingting Wang, Shanghai (CN); Shuhuan Ying, Shanghai (CN)

(73) Assignee: SHANGHAI YONSUN BIOTECHNOLOGY CO., LTD., Shanghai (CN)

( * ) Notice: Subject to any disclaimer, the term of this patent is extended or adjusted under 35 U.S.C. 154(b) by 364 days.

(21) Appl. No.: 18/259,140

(22) PCT Filed: Dec. 20, 2021

(86) PCT No.: PCT/CN2021/139678

§ 371 (c)(1),
(2) Date: Jun. 23, 2023

(87) PCT Pub. No.: WO2022/135343

PCT Pub. Date: Jun. 30, 2022

(65) Prior Publication Data

US 2024/0050363 A1 Feb. 15, 2024

(30) Foreign Application Priority Data

Dec. 23, 2020 (CN) ......................... 202011536858.1

(51) Int. Cl.

| | |
|---|---|
| ***A61K 47/26*** | (2006.01) |
| ***A61K 9/00*** | (2006.01) |
| ***A61K 9/107*** | (2006.01) |
| ***A61K 31/496*** | (2006.01) |
| ***A61K 47/32*** | (2006.01) |
| ***A61K 47/38*** | (2006.01) |

(52) U.S. Cl.
CPC ............ *A61K 9/0019* (2013.01); *A61K 9/107* (2013.01); *A61K 31/496* (2013.01); *A61K 47/26* (2013.01); *A61K 47/32* (2013.01); *A61K 47/38* (2013.01)

(58) Field of Classification Search
CPC ........ A61K 9/146; A61K 9/145; A61K 47/02; A61K 9/10; A61K 9/00; A61K 47/28; A61P 25/24
See application file for complete search history.

(56) References Cited

U.S. PATENT DOCUMENTS

2007/0066601 A1 3/2007 Cremers et al.
2019/0002444 A1 * 1/2019 Iqbal ........................ A61P 25/24

FOREIGN PATENT DOCUMENTS

CN 1893935 A 1/2007
CN 104116741 A * 10/2014
CN 106667939 A 5/2017
EP 3360543 A1 * 8/2018 ........... A61K 9/2054

* cited by examiner

*Primary Examiner* — Robert A Wax
*Assistant Examiner* — Ngoc-Anh Thi Nguyen
(74) *Attorney, Agent, or Firm* — NKL Law; Allen Xue

(57) ABSTRACT

A vilazodone pharmaceutical composition, a preparation method therefor and use thereof are provided. The vilazodone pharmaceutical composition are in vilazodone solid particles. The vilazodone solid particles have a Dv(10) particle size not greater than 20 microns, a Dv(50) particle size not greater than 50 microns and a Dv(90) particle size not greater than 100 microns. The vilazodone pharmaceutical composition has significant advantages such as long-acting sustained release, reducing the frequency of administration, and improving patient compliance.

12 Claims, 11 Drawing Sheets

VILAZODONE PHARMACEUTICAL COMPOSITION, PREPARATION METHOD THEREFOR AND USE THEREOF

CROSS-REFERENCE TO RELATED APPLICATIONS

This application is a U.S. national stage entry of PCT International Application No. PCT/CN2021/139678, filed on Dec. 20, 2021, which claims priority to the prior application with the patent application No. 202011536858.1 titled "VILAZODONE PHARMACEUTICAL COMPOSITION, PREPARATION METHOD THEREFOR AND USE THEREOF" and filed with China National Intellectual Property Administration on Dec. 23, 2020, the content of which is incorporated herein by reference in its entirety.

TECHNICAL FIELD

The present disclosure belongs to the field of pharmaceutical formulations and relates to a vilazodone pharmaceutical composition, a preparation method therefor and use thereof.

BACKGROUND

Depression is a common psychological disease, the signs and symptoms of which include: low mood, aversion to common activities, a significant change in body weight or appetite, insomnia or hypersomnia (somnolence), restlessness/pacing (psychomotor agitation), increased fatigue, a sense of guilt or inferiority, slow thinking or inattention, and, in severe cases, impulses to commit self-harm and suicide. The disease badly affects people's ability to work, sleep, study, eat, and enjoy pleasurable activities.

Low levels of monoamine neurotransmitters such as central norepinephrine (NE), 5-hydroxytryptamine (5-HT), dopamine (DA), etc. and hypofunction of their receptors are believed to be the causes of depression. The initial treatment for depression was electric shock therapy, but the treatment often becomes ineffective after being used several times. At present, there are 3 major classes of drugs for treating depression, one of which is tricyclic antidepressants (TCAs), which can increase the concentration of NE and 5-HT in the brain and have become the standard medications for depression. However, TCAs act slow and have serious adverse effects such as cardiotoxicity. The second class of antidepressants are monoamine oxidase inhibitors (MAOIs), which can retard the degradation of NE and 5-HT in the brain and prolong the duration of action of these transmitters. In the 1980s, a new class of antidepressants, selective serotonin reuptake inhibitors (SSRIs), were developed; they can inhibit the reuptake of 5-HT by the presynaptic membrane, increase the concentration of 5-HT in the synaptic cleft and improve the excitability of the 5-HTIA receptor in the postsynaptic membrane, producing an antidepressant effect. SSRIs are relatively safe in that they do not affect other neurotransmitter receptors. However, SSRIs are less effective than TCAs in treating major depression; in addition, SSRIs non-selectively stimulate various subtypes of 5-HT receptors and therefore have some related adverse effects. Researchers found that buspirone has a high affinity for the $5\text{-}HT_{1A}$ receptor. This finding encouraged the development of selective $5\text{-}HT_{1A}$ receptor agonist-based antidepressants.

Vilazodone hydrochloride (2-benzofurancarboxamide, 5-[4-[4-(5-cyano-1H-indol-3-yl)butyl]-1-piperazinyl] hydrochloride (1:1)) has a molecular formula of $C_{26}H_{27}N502 \cdot HC1$ and a molecular weight of 477.99. The chemical structural formula of the compound is shown below:

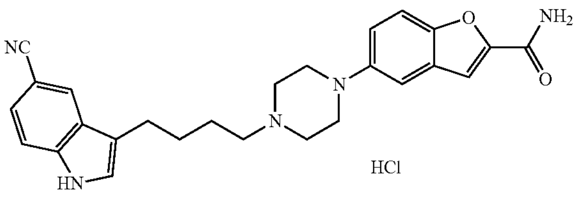 [SMILES: N#Cc1ccc2[nH]cc(CCCCN3CCN(c4ccc5oc(C(N)=O)cc5c4)CC3)c2c1 ; Cl]

On Jan. 21, 2011, the U.S. Food and Drug Administration (FDA) approved the use of vilazodone hydrochloride (trade name: Viibryd) general tablets for treating major depression in adults. Viibryd is manufactured by PGxHealth, New Haven Conn. Vilazodone hydrochloride is a dual-activity drug acting as a 5-hydroxytryptamine 1A ($5\text{-}HT_{1A}$) partial agonist and a selective 5-hydroxytryptamine (5-HT) reuptake inhibitor (SSRI), and it is also the first indolealkylamine-based novel antidepressant. At present, the vilazodone hydrochloride dosage forms sold outside of China come in the following strengths: 10 mg, 20 mg and 40 mg. However, such small-dose tablets have the disadvantages of requiring frequent administration, being hard to orally take, having an unpleasant smell that affects patient compliance, etc. Therefore, the search for a pharmaceutical composition that releases vilazodone in a sustained way, requires less frequent administration and improves patient compliance is an urgent technical problem that needs to be addressed at present.

SUMMARY

To ease the technical problem described above, the present disclosure provides a vilazodone pharmaceutical composition comprising solid particles of vilazodone. The solid particles of vilazodone have the following particle sizes: a Dv(10) of no more than 20 micrometers, a Dv(50) of no more than 50 micrometers and a Dv(90) of no more than 100 micrometers.

According to an embodiment of the present disclosure, the solid particles of vilazodone may be selected from solid particles of vilazodone, a pharmaceutically acceptable salt (such as a hydrochloride) and a solvate thereof.

According to an embodiment of the present disclosure, the solid particles of vilazodone may have the following particle size: a Dv(10) of no more than 10 micrometers or no more than 8 micrometers, for example, 0.1-8 micrometers such as 0.1 micrometers, 0.2 micrometers, 0.5 micrometers, 1 micrometer, 2 micrometers, 3 micrometers, 4 micrometers, 5 micrometers, 6 micrometers, 7 micrometers or 8 micrometers; an example thereof may be 7.187 micrometers, 147.16 nanometers, 4.813 micrometers, 5.522 micrometers, 0.808 micrometers, 187.63 nanometers, 0.873 micrometers, 4.517 micrometers, 6.708 micrometers, 7.483 micrometers, 4.737 micrometers, 4.759 micrometers, 2.105 micrometers or 8.4 micrometers.

According to an embodiment of the present disclosure, the solid particles of vilazodone may have the following particle size: a Dv(50) of no more than 40 micrometers or no more than 30 micrometers, for example, 0.1-30 micrometers such as 0.1 micrometers, 0.2 micrometers, 0.5 micrometers, 1 micrometer, 2 micrometers, 3 micrometers, 4 micrometers, 5 micrometers, 6 micrometers, 7 micrometers, 8 micrometers, 9 micrometers, 10 micrometers, 11 micrometers, 12 micrometers, 13 micrometers, 14 micrometers, 15 micrometers, 16 micrometers, 17 micrometers, 18 micrometers, 19 micrometers, 20 micrometers, 21 micrometers, 22 micrometers, 23 micrometers, 24 micrometers, 25 micrometers, 26 micrometers, 27 micrometers, 28 micrometers, 29 micrometers or 30 micrometers; an example thereof may be 17.245 micrometers, 322.47 nanometers, 25.913 micrometers, 13.825 micrometers, 1.210 micrometers, 296.41 nanometers, 1.550 micrometers, 17.141 micrometers, 17.84 micrometers, 9.745 micrometers or 20.6 micrometers.

According to an embodiment of the present disclosure, the solid particles of vilazodone may have the following particle size: a Dv(90) of no more than 80 micrometers or no more than 50 micrometers, for example, 0.1-50 micrometers such as 0.1 micrometers, 0.2 micrometers, 0.5 micrometers, 1 micrometer, 2 micrometers, 3 micrometers, 4 micrometers, 5 micrometers, 6 micrometers, 7 micrometers, 8 micrometers, 9 micrometers, 10 micrometers, 11 micrometers, 12 micrometers, 13 micrometers, 14 micrometers, 15 micrometers, 16 micrometers, 17 micrometers, 18 micrometers, 19 micrometers, 20 micrometers, 21 micrometers, 22 micrometers, 23 micrometers, 24 micrometers, 25 micrometers, 26 micrometers, 27 micrometers, 28 micrometers, 29 micrometers, 30 micrometers, 31 micrometers, 32 micrometers, 33 micrometers, 34 micrometers, 35 micrometers, 36 micrometers, 37 micrometers, 38 micrometers, 39 micrometers, 40 micrometers, 41 micrometers, 42 micrometers, 43 micrometers, 44 micrometers, 45 micrometers, 46 micrometers, 47 micrometers, 48 micrometers, 49 micrometers or 50 micrometers; an example thereof may be 34.657 micrometers, 707.18 nanometers, 70.580 micrometers, 24.728 micrometers, 1.744 micrometers, 468.23 nanometers, 2.597 micrometers, 72.399 micrometers, 57.063 micrometers, 39.93 micrometers or 43.9 micrometers.

According to an embodiment of the present disclosure, the vilazodone pharmaceutical composition may further comprise a vehicle. The vehicle may be a non-oily vehicle or an oily vehicle. The non-oily vehicle includes, but is not limited to, water. The water may be conventional commercially available water for injection, and is preferably sterile water for injection. The oily vehicle includes, but is not limited to, one or more selected from castor oil, triglyceride, cottonseed oil, sesame oil, and the like.

According to an embodiment of the present disclosure, the vilazodone pharmaceutical composition may further comprise one or more selected from the following: a suspending agent, a wetting agent, an osmotic pressure regulator, a solvent, a stabilizer, a buffer, a pH regulator, a surfactant, a polymer, an electrolyte and a non-electrolyte. The polymer may be a cross-linked polymer and/or a non-cross-linked polymer.

According to an embodiment of the present disclosure, the suspending agent includes, but is not limited to, one or more selected from sodium carboxymethylcellulose, polyethylene glycol and povidone.

According to an embodiment of the present disclosure, the wetting agent includes, but is not limited to, one or more selected from poloxamer, povidone, docusate sodium, sodium deoxycholate and tween.

The tween may be a conventional commercially available tween reagent, such as one or more selected from tween 20 and tween 80.

According to an embodiment of the present disclosure, the osmotic pressure regulator includes, but is not limited to, one or more selected from sodium chloride, mannitol and sucrose.

According to an embodiment of the present disclosure, the solvent includes, but is not limited to, water for injection.

According to an embodiment of the present disclosure, the stabilizer includes, but is not limited to, one or more selected from an antioxidant, a metal ion chelating agent, polyethylene oxide (PEO), polyethylene oxide derivatives, polysorbate, sodium deoxycholate, docusate sodium, poloxamer, polyethoxylated vegetable oil, polyethoxylated castor oil, sorbitan palmitate, lecithin, polyvinyl alcohol, human serum albumin, polyvinylpyrrolidone, povidone, polyethylene glycol, sodium chloride, calcium chloride, dextrose, glycerol, mannitol, and a cross-linked polymer. The antioxidant includes, but is not limited to, one or more selected from citric acid, vitamin C and vitamin E. The metal ion chelating agent includes, but is not limited to, ethylenediaminetetraacetic acid (EDTA). The poloxamer includes, but is not limited to, one or more selected from poloxamer 188, poloxamer 124 and poloxamer 407. The polysorbate includes, but is not limited to, one or more selected from polysorbate 80 and polysorbate 20. The povidone includes, but is not limited to, one or more selected from polyvidone K12, polyvidone K17, PLASDONETM C-12 polyvidone, PLASDONETM C-17 polyvidone, and PLASDONETM C-30 polyvidone. The polyethylene glycol includes, but is not limited to, polyethylene glycol 3350. The cross-linked polymer includes, but is not limited to, sodium carboxymethylcellulose.

According to an embodiment of the present disclosure, the buffer includes, but is not limited to, a buffer selected from phosphoric acid, phosphate, citric acid, sodium citrate, tris(hydroxymethyl)aminomethane (Tris), sodium hydroxide, hydrochloric acid (HCl) and a mixture thereof.

According to an embodiment of the present disclosure, the pH regulator includes, but is not limited to, phosphoric acid, phosphate, citric acid, sodium citrate, hydrochloric acid and sodium hydroxide.

According to an embodiment of the present disclosure, the phosphate includes, but is not limited to, one or more selected from sodium dihydrogen phosphate, disodium hydrogen phosphate, anhydrates or hydrates of sodium dihydrogen phosphate, anhydrates or hydrates of disodium hydrogen phosphate, such as one or more selected from disodium hydrogen phosphate monohydrate ($Na_2HPO_4 \cdot H_2O$), disodium hydrogen phosphate dihydrate ($Na_2HPO_4 \cdot 2H_2O$), anhydrous disodium hydrogen phosphate (anhydrous $Na_2HPO_4$), sodium dihydrogen phosphate monohydrate ($NaH_2PO_4 \cdot H_2O$), sodium dihydrogen phosphate dihydrate ($NaH_2PO_4 \cdot 2H_2O$), and anhydrous sodium dihydrogen phosphate (anhydrous $NaH_2PO_4$).

According to an embodiment of the present disclosure, the co-solvent includes, but is not limited to, one or more selected from ethanol and propylene glycol.

In the vilazodone pharmaceutical composition, the solid particles of vilazodone may have a weight fraction of 1.00-50.00% or 2.00-45.00%, such as 2.00%, 3.00%, 4.00%, 5.00%, 6.00%, 7.00%, 8.00%, 9.00%, 10.00%, 11.00%, 12.00%, 13.00%, 14.00%, 15.00%, 16.00%, 17.00%, 18.00%, 19.00%, 20.00%, 21.00%, 22.00%, 23.00%, 24.00%, 25.00%, 30.00%, 35.00%, 40.00% or 45.00%; an example thereof may be 5.00% or 30.00%; the weight fraction refers to the percentage of the weight of the solid particles of vilazodone to the total weight of the vilazodone pharmaceutical composition. In the vilazodone pharmaceutical composition, the wetting agent may have a weight fraction of 0-5.00%, such as 1.00%, 2.00%, 3.00%, 4.00% or 5.00%, for example, 1.00%; the weight fraction refers to the percentage of the weight of the surfactant to the total weight of the vilazodone pharmaceutical composition.

In the vilazodone pharmaceutical composition, the osmotic pressure regulator may have a weight fraction of 0-5.00%, such as 0, 1.00%, 2.00%, 3.00%, 4.00% or 5.00%, for example, 2.15%; the weight fraction refers to the percentage of the weight of the osmotic pressure regulator to the total weight of the vilazodone pharmaceutical composition.

In the vilazodone pharmaceutical composition, the buffer may have a weight fraction of 0-1.00%, such as 0, 0.10%, 0.20%, 0.30%, 0.40%, 0.50%, 0.60%, 0.70%, 0.80%, 0.90% or 1.00%; the weight fraction refers to the percentage of the weight of the buffer to the total weight of the vilazodone pharmaceutical composition.

In the vilazodone pharmaceutical composition, the stabilizer may have a weight fraction of 0-1.00%, such as 0, 0.10%, 0.20%, 0.30%, 0.40%, 0.50%, 0.60%, 0.70%, 0.80%, 0.90% or 1.00%, for example, 0.60%; the weight fraction refers to the percentage of the weight of the stabilizer to the total weight of the vilazodone pharmaceutical composition.

In the vilazodone pharmaceutical composition, the pH regulator may be used in such an amount that the pH of the composition solution is adjusted to 6.5-8.0, such as 6.6, 6.7, 6.8, 6.9, 7.0, 7.1, 7.2, 7.3, 7.4, 7.5, 7.6, 7.7, 7.8, 7.9 or 8.0, for example, 7.4.

The vilazodone pharmaceutical composition may comprise the following components in percentage by weight: 1.00-50.00% solid particles of vilazodone, 0-5.00% wetting agent, 0-5.00% stabilizer, 0-5.00% osmotic pressure regulator, 0-1.00% buffer salt and solvent.

Or as an option, the vilazodone pharmaceutical composition may comprise the solid particles of vilazodone in a weight/volume (g/mL) percentage amount of 1.00-50.00% or 2.00-45.00%, such as 2.00%, 3.00%, 4.00%, 5.00%, 6.00%, 7.00%, 8.00%, 9.00%, 10.00%, 11.00%, 12.00%, 13.00%, 14.00%, 15.00%, 16.00%, 17.00%, 18.00%, 19.00%, 20.00%, 21.00%, 22.00%, 23.00%, 24.00%, 25.00%, 30.00%, 35.00%, 40.00% or 45.00%; an example thereof may be 5.00% or 30.00%.

The vilazodone pharmaceutical composition may comprise the wetting agent in a weight/volume (g/mL) percentage amount of 0-5.00%, such as 1.00%, 2.00%, 3.00%, 4.00% or 5.00%, for example, 1.00%, wherein the percentage refers to the mass/volume percentage (g/mL) of the weight of the component to the volume of the vilazodone pharmaceutical composition.

The vilazodone pharmaceutical composition may comprise the osmotic pressure regulator in a weight/volume (g/mL) percentage amount of 0-5.00%, such as 0, 1.00%, 2.00%, 3.00%, 4.00% or 5.00%, for example, 2.15%, wherein the percentage refers to the mass/volume percentage (g/mL) of the weight of the component to the volume of the vilazodone pharmaceutical composition.

The vilazodone pharmaceutical composition may comprise the buffer in a weight/volume (g/mL) percentage amount of 0-1.00%, such as 0, 0.10%, 0.20%, 0.30%, 0.40%, 0.50%, 0.60%, 0.70%, 0.80%, 0.90% or 1.00%, wherein the percentage refers to the mass/volume percentage (g/mL) of the weight of the component to the volume of the vilazodone pharmaceutical composition.

The vilazodone pharmaceutical composition may comprise the stabilizer in a weight/volume (g/mL) percentage amount of 0-1.00%, such as 0, 0.10%, 0.20%, 0.30%, 0.40%, 0.50%, 0.60%, 0.70%, 0.80%, 0.90% or 1.00%, for example, 0.60%, wherein the percentage refers to the mass/volume percentage (g/mL) of the weight of the component to the volume of the vilazodone pharmaceutical composition.

In the vilazodone pharmaceutical composition, the pH regulator may be used in such an amount that the pH of the composition solution is adjusted to 6.5-8.0, such as 6.6, 6.7, 6.8, 6.9, 7.0, 7.1, 7.2, 7.3, 7.4, 7.5, 7.6, 7.7, 7.8, 7.9 or 8.0, for example, 7.4.

The vilazodone pharmaceutical composition may comprise the following components in weight/volume (g/mL) percentage: 1.00-50.00% solid particles of vilazodone, 0-5.00% wetting agent, 0-5.00% stabilizer, 0-5.00% osmotic pressure regulator, 0-1.00% buffer salt and solvent, wherein the percentage refers to the mass/volume percentage (g/mL) of the weight of each component to the volume of the vilazodone pharmaceutical composition.

According to an embodiment of the present disclosure, the vilazodone pharmaceutical composition may be selected from one of the following formulas:

formula a: 30% vilazodone hydrochloride, 1% tween 20, 2.15% mannitol, 0.08% anhydrous sodium dihydrogen phosphate, and 0.4% anhydrous disodium hydrogen phosphate, with the balance preferably being water, wherein the percentage refers to the percentage of the weight of each component to the total weight of the vilazodone pharmaceutical composition;

formula b: 5% vilazodone hydrochloride, 1% tween 20, 0.3% PVPK12, and 0.3% sodium deoxycholate, with the balance preferably being water, wherein the percentage refers to the percentage of the weight of each component to the total weight of the vilazodone pharmaceutical composition;

formula c: 20% vilazodone hydrochloride, 1% tween 20, 0.3% PVPk12, 0.3% sodium deoxycholate, 0.45% disodium hydrogen phosphate, 0.09% sodium dihydrogen phosphate, 2.5% mannitol, and 0.18% sodium carboxymethylcellulose, with the balance preferably being water, wherein the percentage refers to the percentage of the weight of each component to the total weight of the vilazodone pharmaceutical composition;

formula d: 36.3% vilazodone hydrochloride, 0.91% tween 20, 0.34% disodium hydrogen phosphate, 0.07% sodium dihydrogen phosphate, 2.0% mannitol, and 0.21% sodium carboxymethylcellulose, with the balance preferably being water, wherein the percentage refers to the percentage of the weight of each component to the total weight of the vilazodone pharmaceutical composition;

formula e: 30% vilazodone hydrochloride, 1% tween 20, 0.38% disodium hydrogen phosphate, 0.08% sodium dihydrogen phosphate, 2.20% mannitol, and 0.23% sodium carboxymethylcellulose, with the balance preferably being water, wherein the percentage refers to the percentage of the weight of each component to the total weight of the vilazodone pharmaceutical composition;

formula f: 30-40% vilazodone hydrochloride, 1% tween 20, 0-0.3% PVP K12, 0.33-0.39% disodium hydrogen phosphate, 0.07-0.08% sodium dihydrogen phosphate, 1.6-2.2% mannitol, and 0-1.0% sodium carboxymethylcellulose, with the balance preferably being water, wherein the percentage refers to the percentage of the weight of each component to the total weight of the vilazodone pharmaceutical composition;

formula av: 30% vilazodone hydrochloride, 1% tween 20, 2.15% mannitol, 0.08% anhydrous sodium dihydrogen phosphate, and 0.4% anhydrous disodium hydrogen phosphate, with the balance preferably being water, wherein the percentage refers to the mass/volume percentage (g/mL) of the weight of each component to the volume of the vilazodone pharmaceutical composition;

formula by: 5% vilazodone hydrochloride, 1% tween 20, 0.3% PVPK12, and 0.3% sodium deoxycholate, with the balance preferably being water, wherein the percentage refers to the mass/volume percentage (g/mL) of the weight of each component to the volume of the vilazodone pharmaceutical composition;

formula cv: 20% vilazodone hydrochloride, 1% tween 20, 0.3% PVPk12, 0.3% sodium deoxycholate, 0.45% disodium hydrogen phosphate, 0.09% sodium dihydrogen phosphate, 2.5% mannitol, and 0.18% sodium carboxymethylcellulose, with the balance preferably being water, wherein the percentage refers to the mass/volume percentage (g/mL) of the weight of each component to the volume of the vilazodone pharmaceutical composition;

formula dv: 36.3% vilazodone hydrochloride, 0.91% tween 20, 0.34% disodium hydrogen phosphate, 0.07% sodium dihydrogen phosphate, 2.0% mannitol, and 0.21% sodium carboxymethylcellulose, with the balance preferably being water, wherein the percentage refers to the mass/volume percentage (g/mL) of the weight of each component to the volume of the vilazodone pharmaceutical composition;

formula ev: 30% vilazodone hydrochloride, 1% tween 20, 0.38% disodium hydrogen phosphate, 0.08% sodium dihydrogen phosphate, 2.20% mannitol, and 0.23% sodium carboxymethylcellulose, with the balance preferably being water, wherein the percentage refers to the mass/volume percentage (g/mL) of the weight of each component to the volume of the vilazodone pharmaceutical composition; and formula fv: 30-40% vilazodone hydrochloride, 1% tween 20, 0-0.3% PVP K12, 0.33-0.39% disodium hydrogen phosphate, 0.07-0.08% sodium dihydrogen phosphate, 1.6-2.2% mannitol, and 0-1.0% sodium carboxymethylcellulose, with the balance preferably being water, wherein the percentage refers to the mass/volume percentage (g/mL) of the weight of each component to the volume of the vilazodone pharmaceutical composition.

According to an embodiment of the present disclosure, the vilazodone pharmaceutical composition has a ratio of sedimental volume $(H/H_0)$ of 0.8 or above, such as, 0.8-1.0, for example, 0.81-0.99, preferably greater than 0.8.

The present disclosure also provides a preparation method for the vilazodone pharmaceutical composition, which comprises the following steps:

step 1: mixing the solid particles of vilazodone with other components in a formula to obtain a premix; and step 2: grinding the premix obtained in step 1 together with zirconium beads to obtain the vilazodone pharmaceutical composition.

In step 1, the mixing is preferably mixing by stirring.

In step 2, the zirconium beads may have a particle size of 0.01-2 mm, such as 0.1 mm, 0.3 mm, 0.6 mm or 1 mm, for example, 0.3 mm.

In step 2, the zirconium beads and the premix are preferably in a volume ratio of 1-5, such as 1, 1.5, 2 or 3, for example, 1.5.

In step 2, the grinding may be performed for 1 min to 24 h, or 5 min to 20 h, such as, 5-15 h, for example, 10 h.

According to an embodiment of the present disclosure, the zirconium beads are conventional commercially available zirconium oxide beads.

The present disclosure further provides a pharmaceutical formulation comprising the vilazodone pharmaceutical composition.

The present disclosure further provides use of the vilazodone pharmaceutical composition for manufacturing a medicament, for example, a vilazodone pharmaceutical formulation.

According to an embodiment of the present disclosure, the medicament is a 5-hydroxytryptamine 1A (5-$HT_{1A}$) partial agonist and/or a selective 5-hydroxytryptamine (5-HT) reuptake inhibitor (SSRI); more preferably, the medicament is used for preventing and/or treating depression, for example, major depression in adults.

The vilazodone pharmaceutical formulation includes, but is not limited to, one or more selected from a tablet, a granule, a capsule, a pellet, an oral liquid, an injection, and the like. Preferably, the tablet includes, but is not limited to, one or more selected from a sustained-release tablet, an osmotic pump tablet and an orally disintegrating tablet. Preferably, the injection may be a liquid injection, a powder for injection or a tablet for injection; for example, the liquid injection may be a suspension, such as an aqueous suspension or a powder for suspension; for example, the powder for suspension may be a lyophilized powder injection.

According to an embodiment of the present disclosure, the injection may be a long-acting injection, wherein the long-acting injection may be either an aqueous suspension, or a powder for suspension, which is dispersed in a specific diluent to form a suspension when in use.

According to an embodiment of the present disclosure, the concentration of vilazodone in the long-acting injection is not less than 50 mg/mL.

The present disclosure also provides a vilazodone pharmaceutical formulation comprising the vilazodone pharmaceutical composition described above.

According to an embodiment of the present disclosure, the vilazodone pharmaceutical formulation has a dosage form selection and/or vilazodone concentration as described above.

The present disclosure also provides use of the vilazodone pharmaceutical composition, the medicament and/or the vilazodone pharmaceutical formulation described above as a 5-hydroxytryptamine 1A (5-$HT_{1A}$) partial agonist and/or a selective 5-hydroxytryptamine (5-HT) reuptake inhibitor (SSRI).

The present disclosure also provides use of the vilazodone pharmaceutical composition, the medicament and/or the vilazodone pharmaceutical formulation described above in the prevention and/or treatment of depression, for example, major depression in adults.

The present disclosure further provides a method for preventing and/or treating depression, for example, major depression in adults, which comprises administering the vilazodone pharmaceutical composition, the medicament and/or the vilazodone pharmaceutical formulation described above to a patient, for example, a human, in need thereof.

The present disclosure further provides a method of partially agonizing 5-hydroxytryptamine 1A (5-$HT_{1A}$) and/or selectively inhibiting reuptake of 5-hydroxytryptamine (5-HT), which comprises administering the vilazodone pharmaceutical composition, the medicament and/or the vilazodone pharmaceutical formulation described above to a patient, for example, a human, in need thereof. It is to be understood that, since the active ingredient in the pharmaceutical composition of the present disclosure is vilazodone, a pharmaceutically acceptable salt thereof or a solvate thereof known in the art, the pharmaceutical composition is applicable to diseases or disorders to which vilazodone, the pharmaceutically acceptable salt thereof or the solvate thereof known in the art is applicable.

According to an embodiment of the present disclosure, unless otherwise specified, the "Dv(10)", "Dv(25)", "Dv(50)", "Dv(75)" and "Dv(90)" refer to volume-weighted particle diameters, wherein a cumulative of 10 v/v %, 25 v/v %, 50 v/v %, 75 v/v % or 90 v/v % of the particles have equal or smaller diameters in the measurement. For example, if the Dv(50) of a population of particles is about 25 micrometers, then 50% by volume of the particles have a diameter of less than or equal to about 25 micrometers.

Unless otherwise stated, the particle diameter parameters such as "D(10)", "D(25)", "D(50)", "D(75)" and "D(90)" in the context of the present application all refer to volume-weighted particle diameters, which have the same meaning as "Dv(10)", "Dv(25)", "Dv(50)", "Dv(75)" and "Dv(90)", respectively. The preferred conditions described above may be combined arbitrarily to obtain preferred embodiments of the present disclosure without departing from the general knowledge in the art.

The reagents and starting materials used in the present disclosure are commercially available.

According to an embodiment of the present disclosure, the room temperature refers to an ambient temperature of 10-35° C.

The benefits of the present disclosure: The vilazodone pharmaceutical composition of the present disclosure overcomes the defects in the existing vilazodone hydrochloride tablets, such as requiring frequent administration, being hard to orally take, having an unpleasant smell that affects patient compliance, etc., has significant advantages of releasing the drug in a sustained way, requiring less frequent administration, improving patient compliance, etc., and has a good marketing prospect.

DETAILED DESCRIPTION

The technical solutions of the present disclosure will be further illustrated in detail with reference to the following specific examples. It will be understood that the following examples are merely exemplary illustrations and explanations of the present disclosure, and should not be construed as limiting the protection scope of the present disclosure. All techniques implemented based on the content of the present disclosure described above are included within the protection scope of the present disclosure.

Unless otherwise stated, the starting materials and reagents used in the following examples are all commercially available products or can be prepared using known methods. Experimental procedures without specified conditions in the following examples are conducted in accordance with conventional procedures and conditions, or in accordance with the manufacturer's manual.

Unless otherwise specified, the units of the mass-to-volume ratios (W/V×100%) in the context of the present disclosure are all g/mL; the disodium hydrogen phosphate and sodium dihydrogen phosphate used are both anhydrates, and their proportions are calculated on the basis of the molecular weight of the anhydrates.

Example 1

TABLE 1

The formula for the suspension injection

| Formula 1 | Component (W/V %) |
|---|---|
| Vilazodone hydrochloride | 30 |
| Tween 20 | 1 |
| Mannitol | 2.15 |
| Anhydrous sodium dihydrogen phosphate | 0.08 |
| Anhydrous disodium hydrogen phosphate | 0.4 |
| Sterile water for injection | q.s. 100 |

Figure 1:
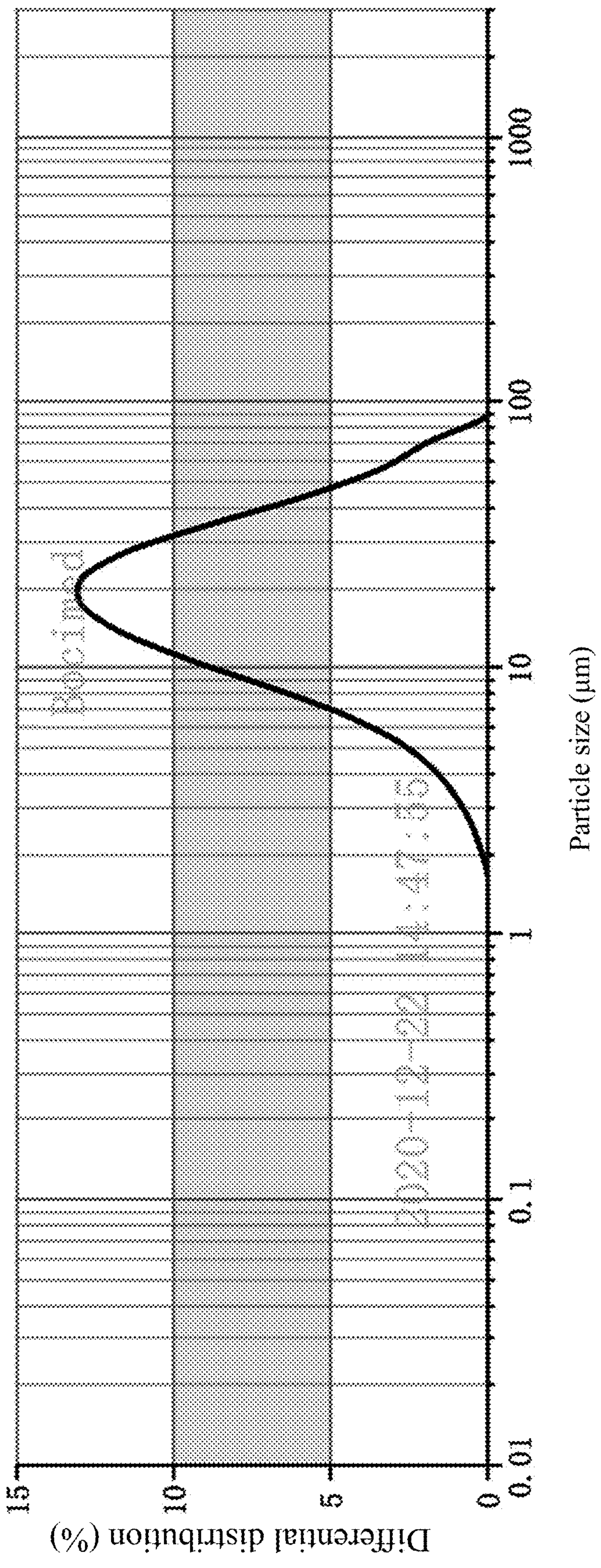
FIG. 1 shows a particle size distribution of solid particles of vilazodone in the suspension in Example 1.
Figure 2:
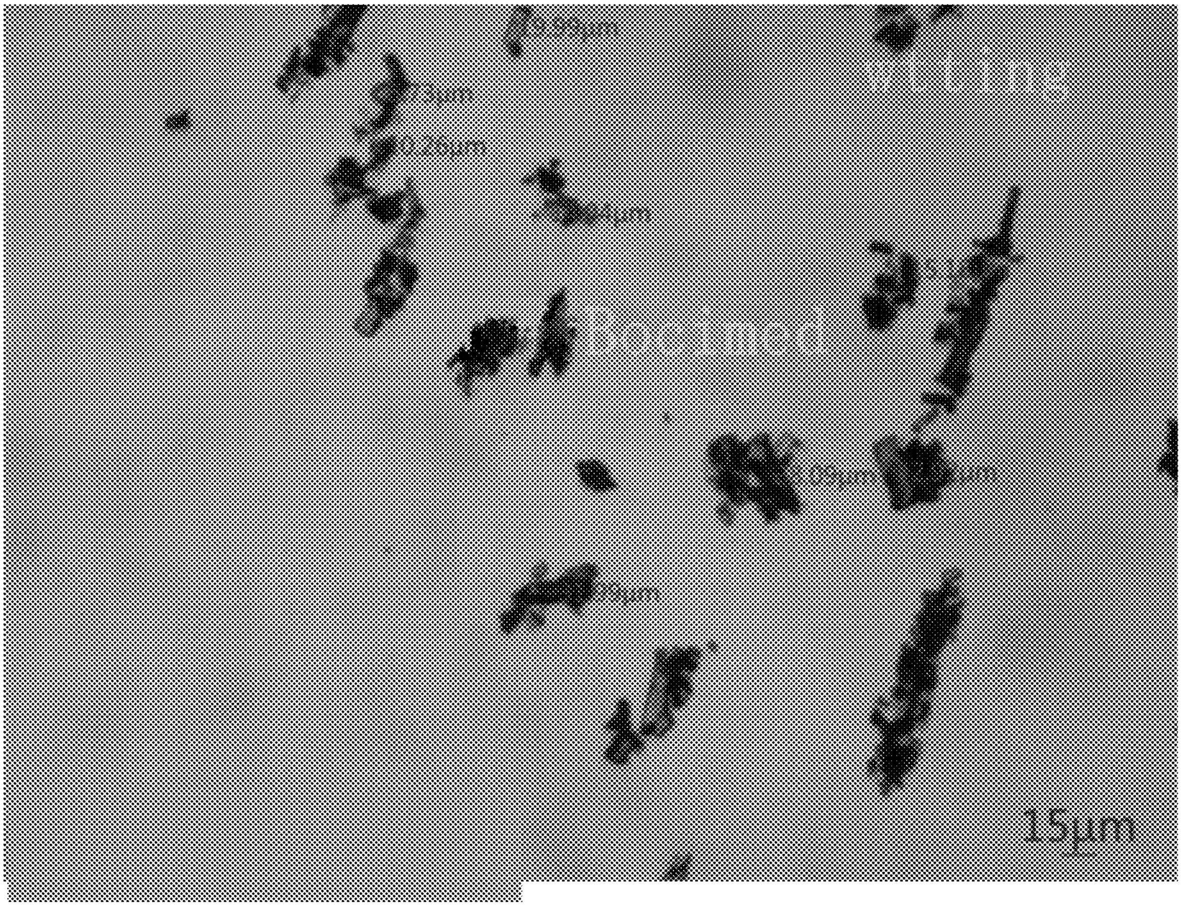
FIG. 2 shows the particle size morphology of solid particles of vilazodone in the suspension in Example 1 under a polarized light microscope, with a scale of 15 micrometers.

According to formula 1 shown in Table 1, the raw and auxiliary materials were weighed out and well mixed to obtain the suspension. The particle size was measured on a laser particle analyzer (parameter settings: dispersion medium: water; refractive index of dispersion medium: 1.333; absorbance of sample material: 0.05; refractive index of sample material: 1.711). The particle size morphology of the particles in the ground suspension was observed under a polarized light microscope. The particle size distribution data of the solid particles of vilazodone in the suspension are shown in Table 2 and FIG. 1. The particle size morphology of the solid particles of vilazodone in the suspension under the polarized light microscope is shown in FIG. 2.

The results show that the morphological size of the particles observed under the polarized light microscope agrees with the particle size measured on the laser particle analyzer. The vilazodone solid in the suspension was a block of about 6-38 μm.

TABLE 2

The particle size distribution of vilazodone in the composition of Example 1

| D10 (μm) | D25 (μm) | D50 (μm) | D75 (μm) | D90 (μm) |
|---|---|---|---|---|
| 7.187 | 11.160 | 17.245 | 25.717 | 34.657 |

Example 2

TABLE 3

The formula for the suspension injection of Example 2

| Component | Ratio (%, W/W) Formula 2 | Ratio (%, W/V) Formula 2 |
|---|---|---|
| Vilazodone hydrochloride | 5 | 5.0 |
| Tween 20 | 1 | 1.1 |
| PVPk12 | 0.3 | 0.3 |
| Sodium deoxycholate | 0.3 | 0.3 |
| Sterile water for injection | q.s. 100 | 93.3 |

According to formula 2 shown in Table 3, the raw and auxiliary materials were weighed out and well mixed by stirring to form a primary suspension. The primary suspension was added to a 1.5-fold volume of 0.3 mm zirconium beads. The mixture was placed in a grinding jar and ground for 10 h to obtain the vilazodone pharmaceutical composition. The grinding was performed in a ball mill, and the parameter settings of the planetary ball mill were as follows: fixed parameters: the diameter of the revolution plate: about 191 mm, the diameter of the rotation cup: about 71 mm, the height of the rotation cup: about 70 mm, the capacity of the rotation cup: 100 mL, the revolution speed of the revolution plate: 10 r/min, and the rotation speed: 720 r/min. The particle size was measured on a nano particle size analyzer (NICOMP Particle Sizing Systems, parameter settings: dispersion medium: water; refractive index of dispersion medium: 1.333; viscosity: 0.933 cp; temperature: 23° C.; luminous intensity setting: 300 kHz).

Figure 3:
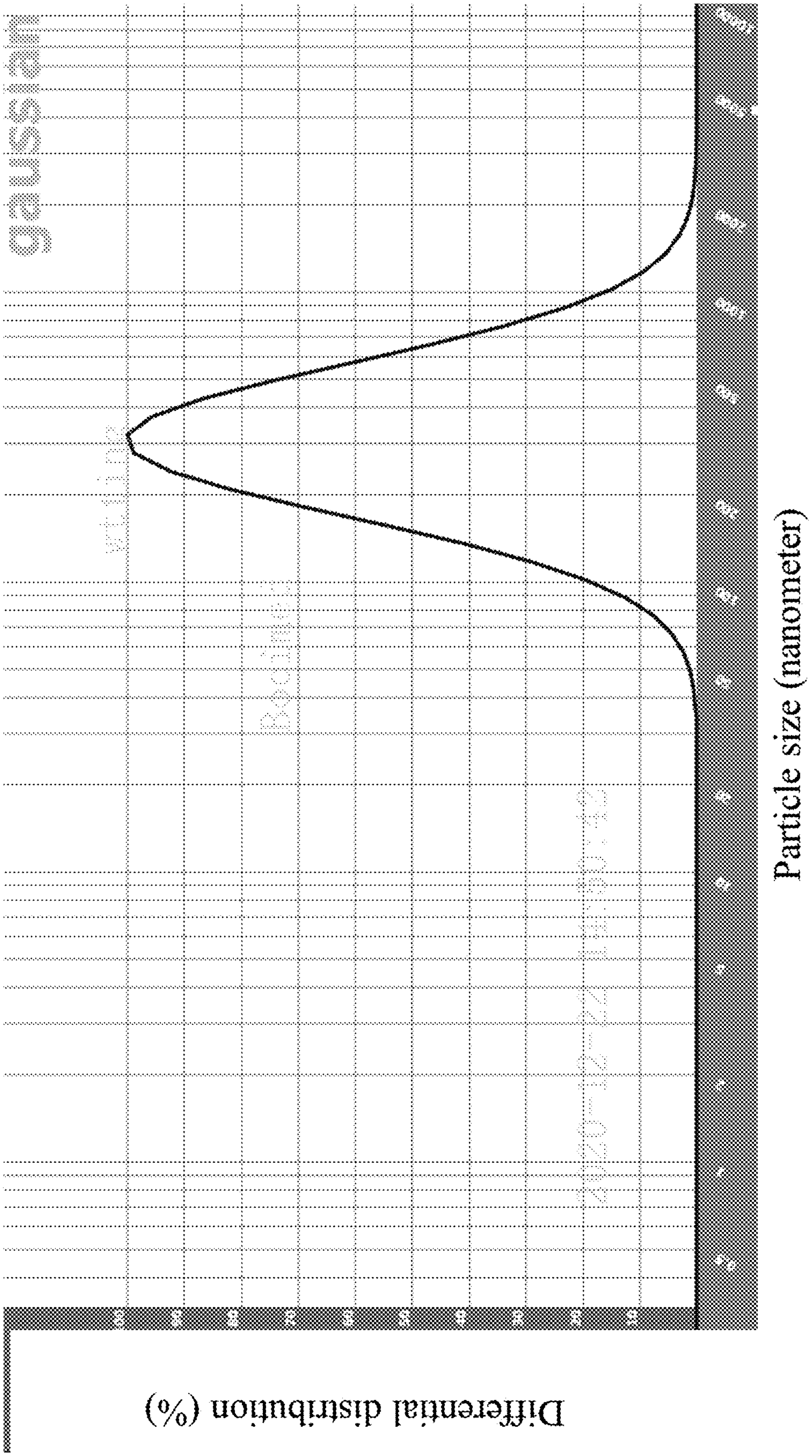
FIG. 3 shows a particle size distribution of solid particles of vilazodone in the suspension in Example 2.

The particle size distribution data of the solid particles of vilazodone in the suspension of formula 2 after 10 h of grinding are shown in Table 4 and FIG. 3.

TABLE 4

The particle size distribution of vilazodone in the suspension

| Particle size distribution | Mean (nm) | Standard deviation (nm) | Polydispersity index (PI) | D10 (nm) | D25 (nm) | D50 (nm) | D75 (nm) | D90 (nm) |
|---|---|---|---|---|---|---|---|---|
| Gaussian distribution luminous intensity weight | 372.54 | 228.41 | 0.376 | 140.90 | 204.21 | 308.66 | 466.62 | 676.86 |
| Gaussian distribution volume weight | 389.25 | 238.66 | 0.376 | 147.16 | 213.33 | 322.47 | 487.52 | 707.18 |
| Gaussian distribution quantity weight | 63.74 | 39.08 | 0.376 | 47.51 | 54.98 | 70.84 | 97.64 | 134.76 |

Example 3

TABLE 4

The formulas for the suspension injections of formulas 3, 4, 5 and 6 of Example 3

| Component | Ratio (%, W/V) Formulas 3, 4, 5 and 6 |
|---|---|
| Vilazodone hydrochloride | 20 |
| Tween 20 | 1 |
| PVPk12 | 0.3 |
| Sodium deoxycholate | 0.3 |
| Disodium hydrogen phosphate | 0.45 |
| Sodium dihydrogen phosphate | 0.09 |
| Mannitol | 2.5 |
| Sodium carboxymethylcellulose | 0.18 |
| Sterile water for injection | q.s. 100 |

According to the formulas shown in Table 4, the raw and auxiliary materials were weighed out and well mixed by stirring to form primary suspensions. The primary suspensions were added to 1.5-fold volumes of 0.6 mm zirconium beads. The mixtures were placed in a grinding jar and ground for 0 min, 5 min, 10 min and 10 h to obtain the vilazodone pharmaceutical compositions of formulas 3, 4, 5 and 6, respectively. The grinding was performed in a ball mill, and the parameter settings of the planetary ball mill were as follows: fixed parameters: the diameter of the revolution plate: about 191 mm, the diameter of the rotation cup: about 71 mm, the height of the rotation cup: about 70 mm, the capacity of the rotation cup: 100 mL, the revolution speed of the revolution plate: 10 r/min, and the rotation speed: 720 r/min.

The particle size of formulas 3, 4 and 5 and the distribution thereof were measured on a laser particle analyzer using the following parameter settings: dispersion medium: water; refractive index of dispersion medium: 1.333; absorbance of sample material: 0.05; refractive index of sample material: 1.711. The particle size and the distribution of formula 6 were measured on a nano particle size analyzer (NICOMP Particle Sizing Systems) using the following parameter settings: dispersion medium: water; refractive index of dispersion medium: 1.333; viscosity: 0.933 cp; temperature: 23° C.; luminous intensity setting: 300 kHz.

Figure 4:
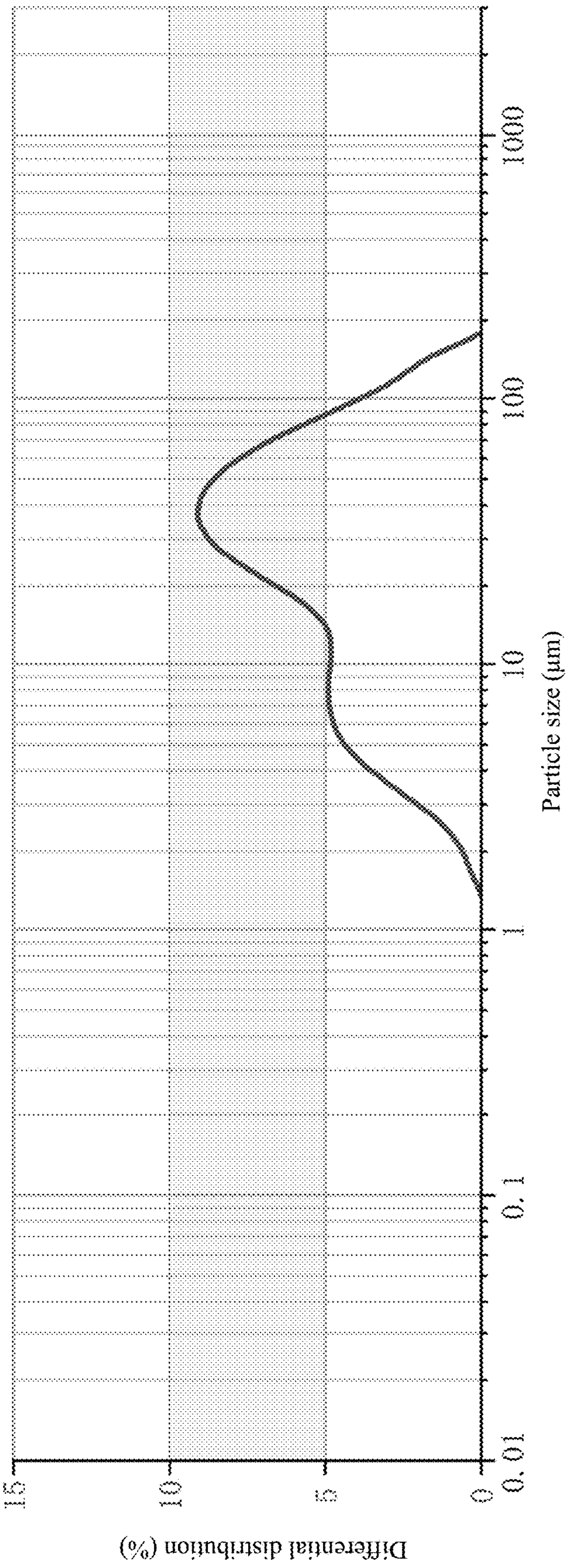
FIG. 4 shows a particle size distribution of solid particles of vilazodone in the suspension of formula 3 in Example 3.
Figure 5:
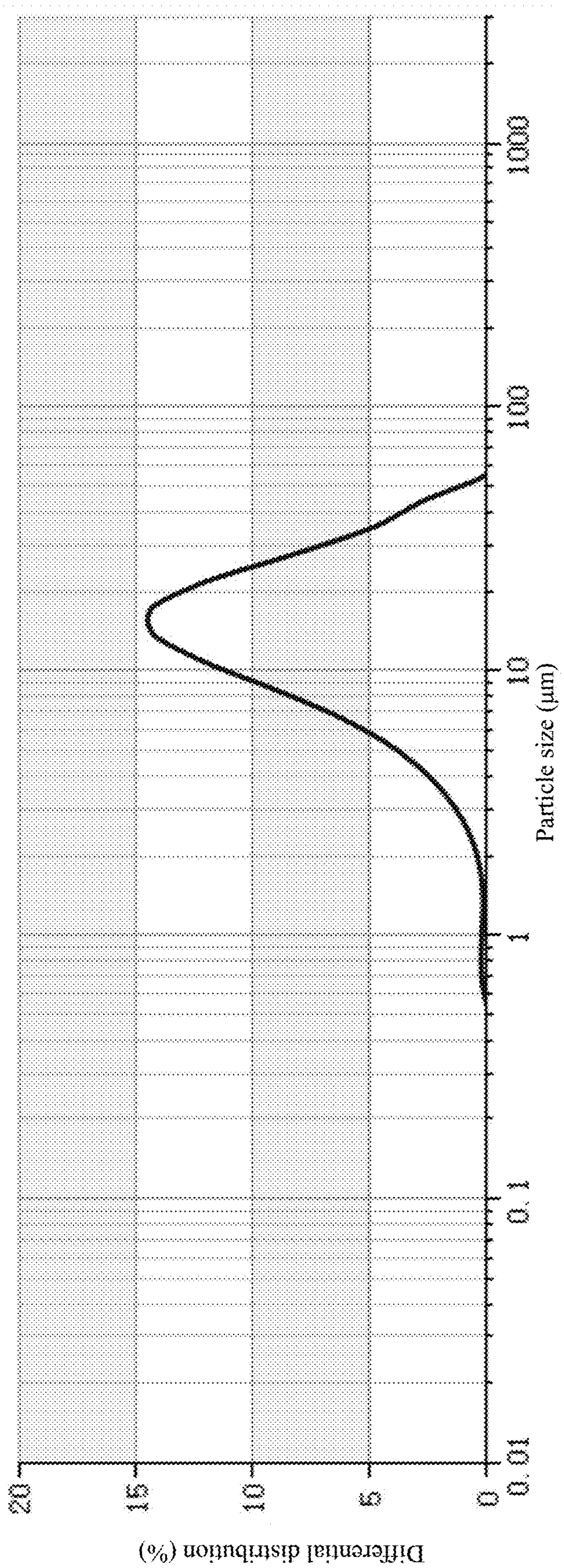
FIG. 5 shows a particle size distribution of solid particles of vilazodone in the suspension of formula 4 in Example 3.
Figure 6:
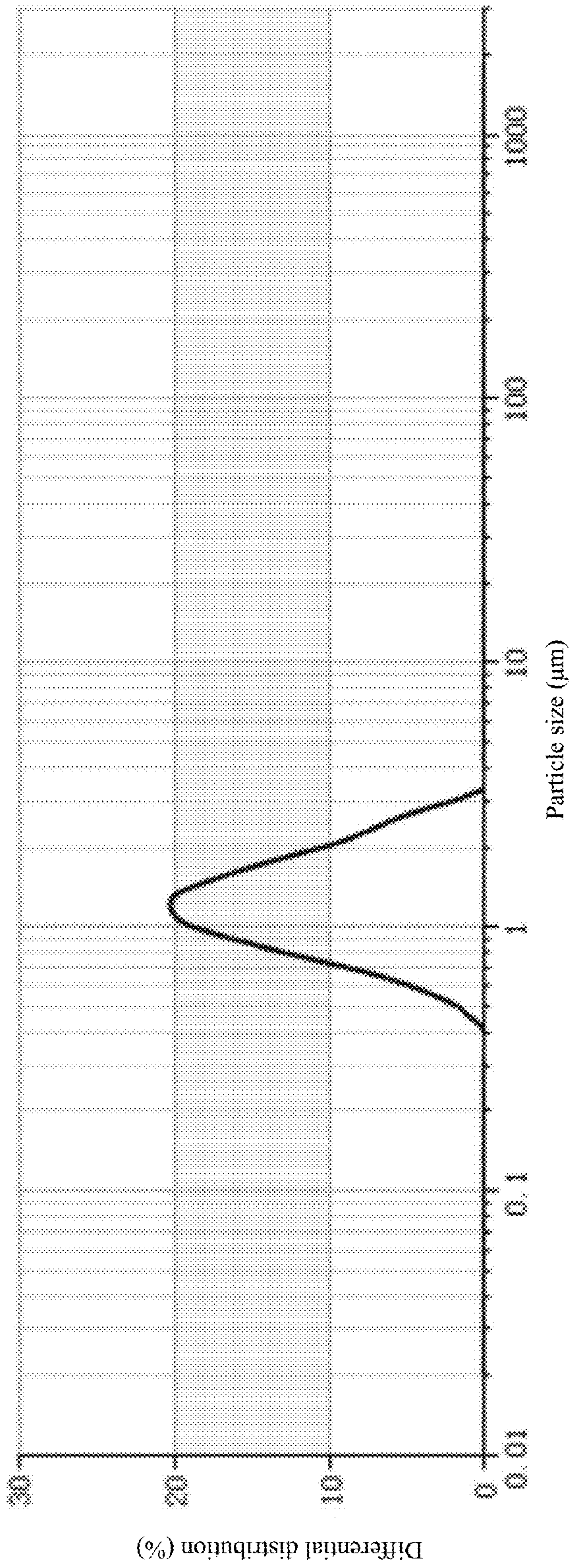
FIG. 6 shows a particle size distribution of solid particles of vilazodone in the suspension of formula 5 in Example 3.
Figure 7:
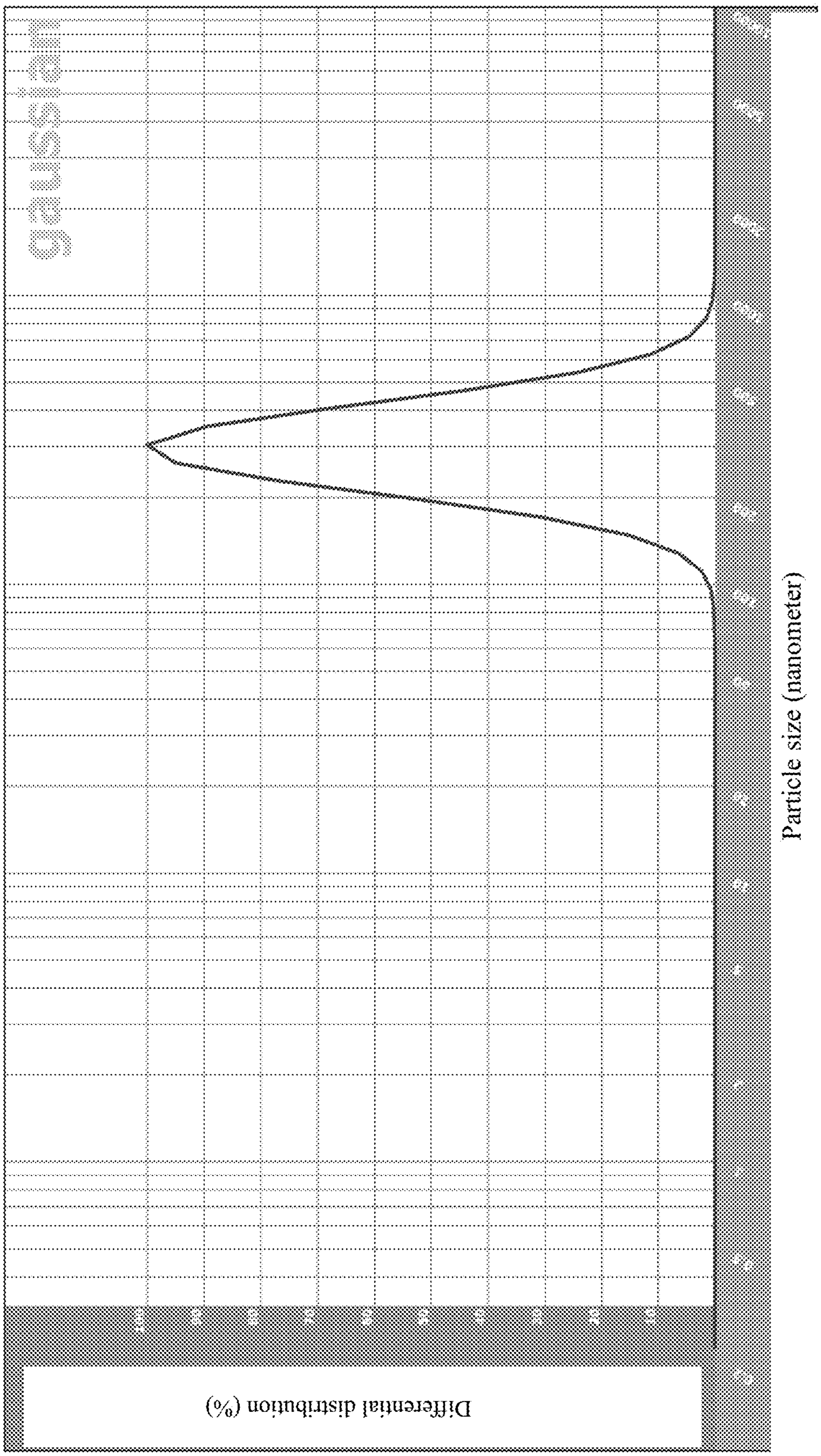
FIG. 7 shows a particle size distribution of solid particles of vilazodone in the suspension of formula 6 in Example 3.

The particle size distribution data of the solid particles of vilazodone in the suspensions of formulas 3, 4 and 5 are shown in Table 5 and FIGS. 4, 5 and 6. The particle size distribution data of the solid particles of vilazodone in the suspension of formula 6 are shown in Table 6 and FIG. 7.

Figure 8:
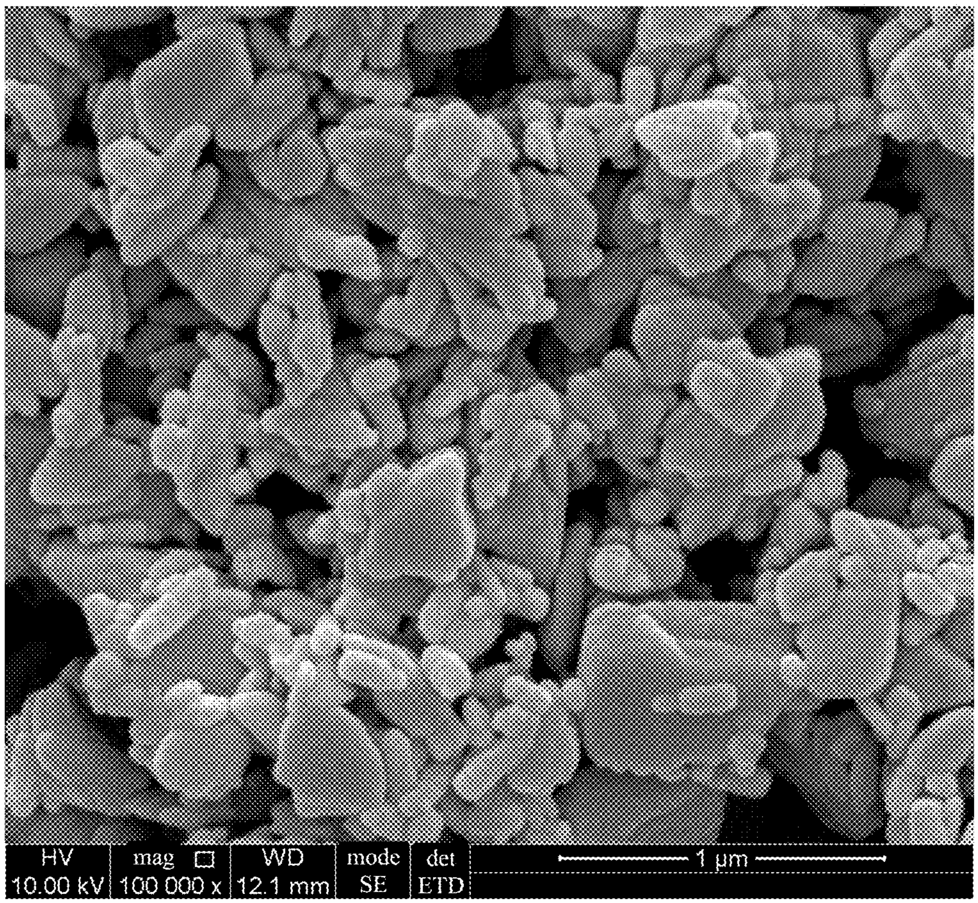
FIG. 8 shows an electron micrograph of solid particles of vilazodone in the suspension of formula 6 in Example 3.
Figure 9:
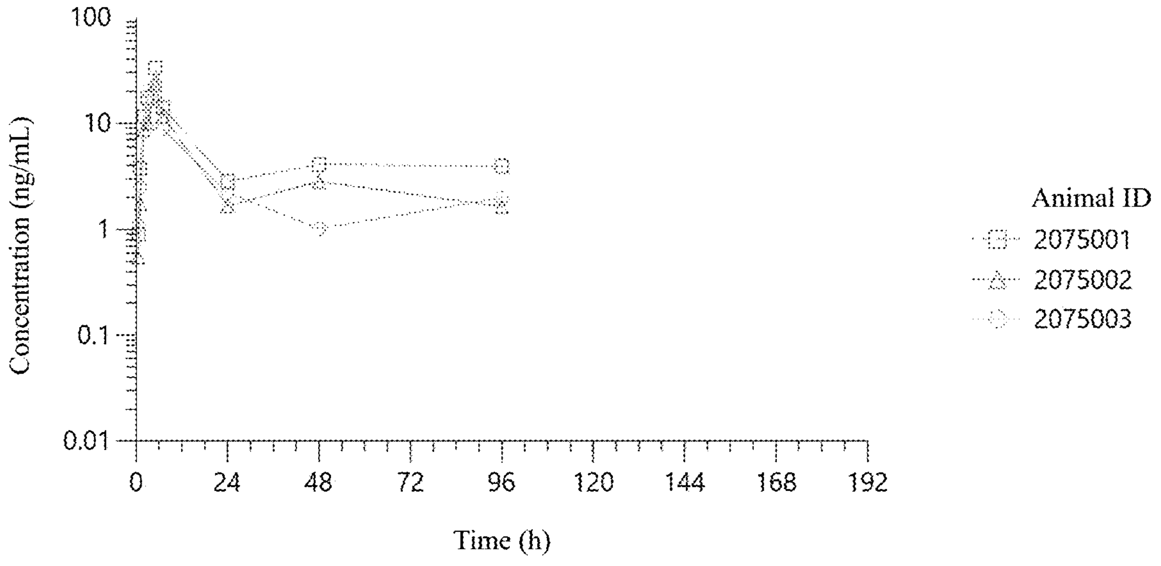
FIG. 9 shows drug concentration-time curves in the animals in group G1 in Example 4 after vilazodone administration.
Figure 10:
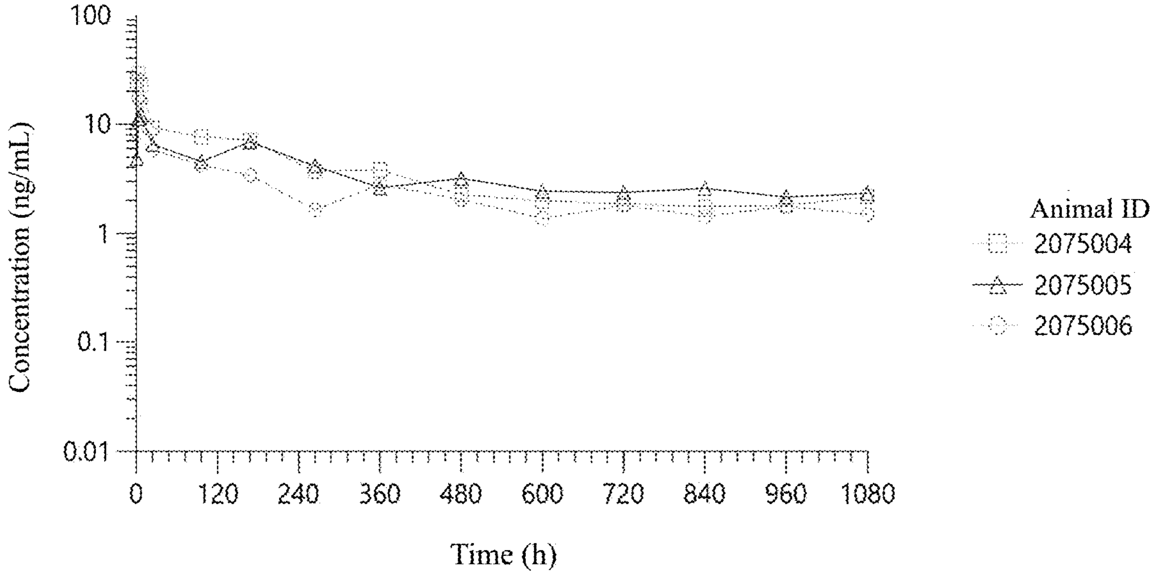
FIG. 10 shows drug concentration-time curves in the animals in group G2 in Example 4 after vilazodone administration.
Figure 11:
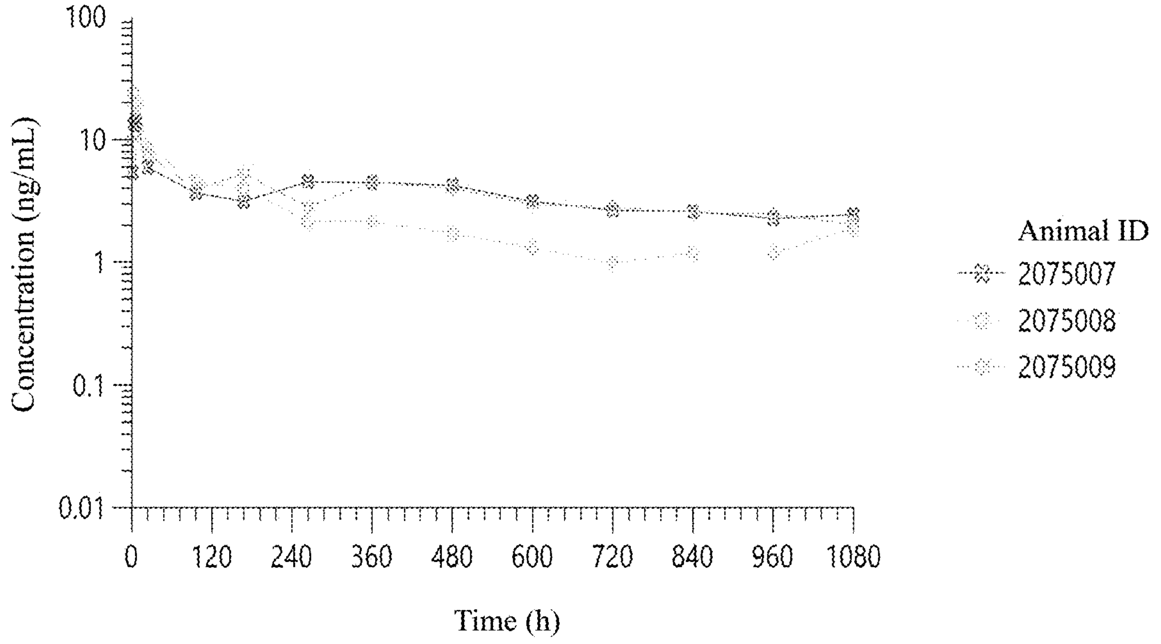
FIG. 11 shows drug concentration-time curves in the animals in group G3 in Example 4 after vilazodone administration.
Figure 12:
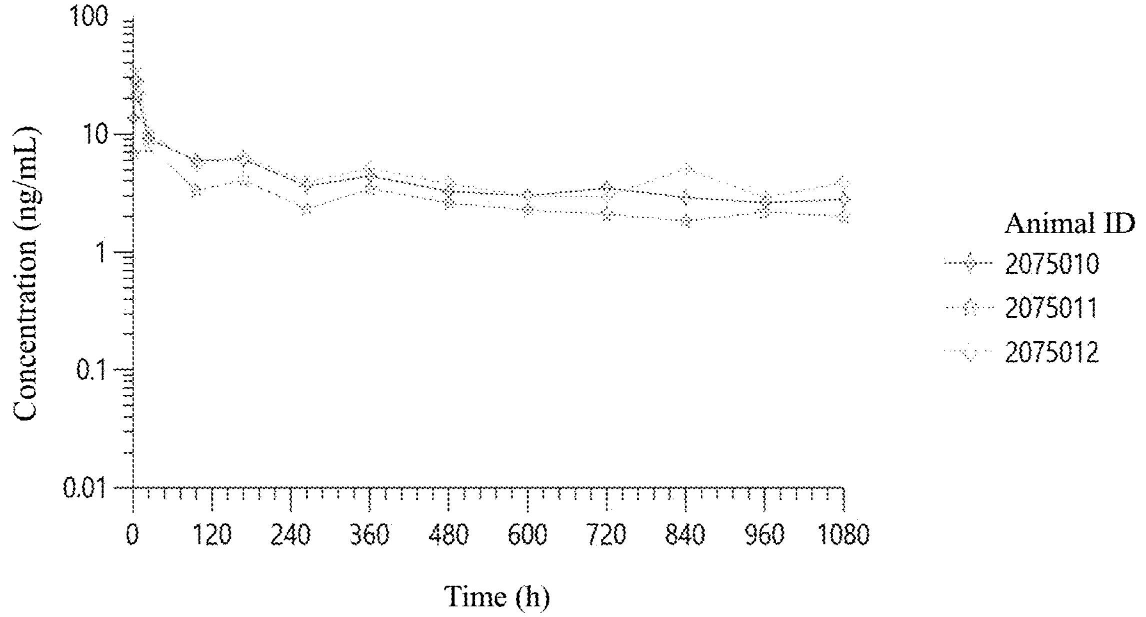
FIG. 12 shows drug concentration-time curves in the animals in group G4 in Example 4 after vilazodone administration.
Figure 13:
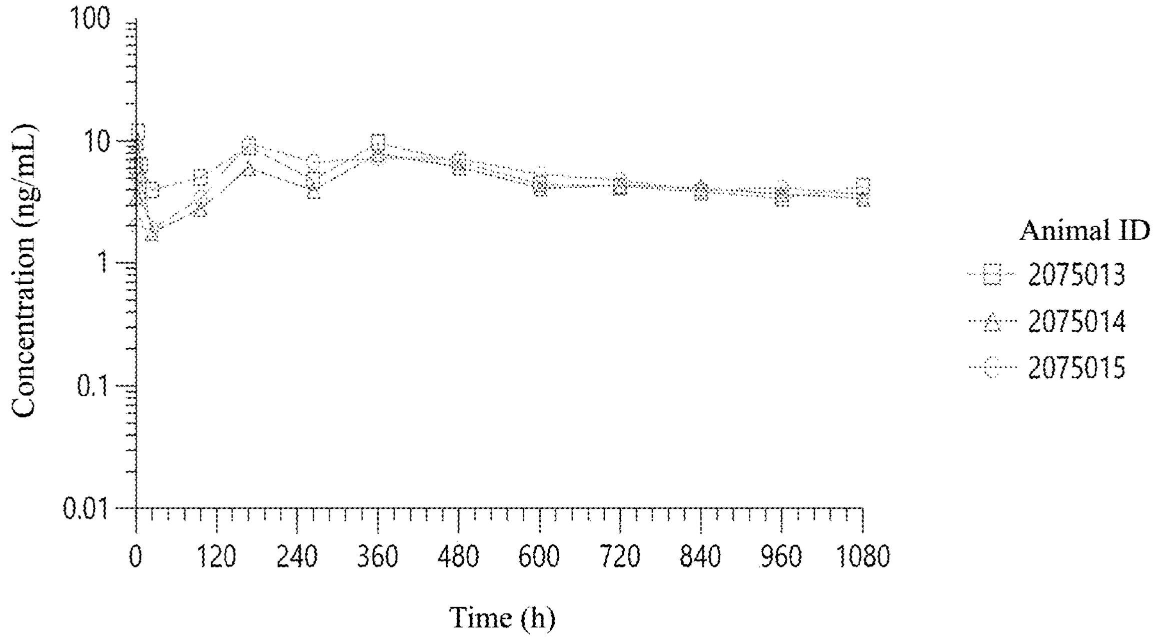
FIG. 13 shows drug concentration-time curves in the animals in group G5 in Example 4 after vilazodone administration.
Figure 14:
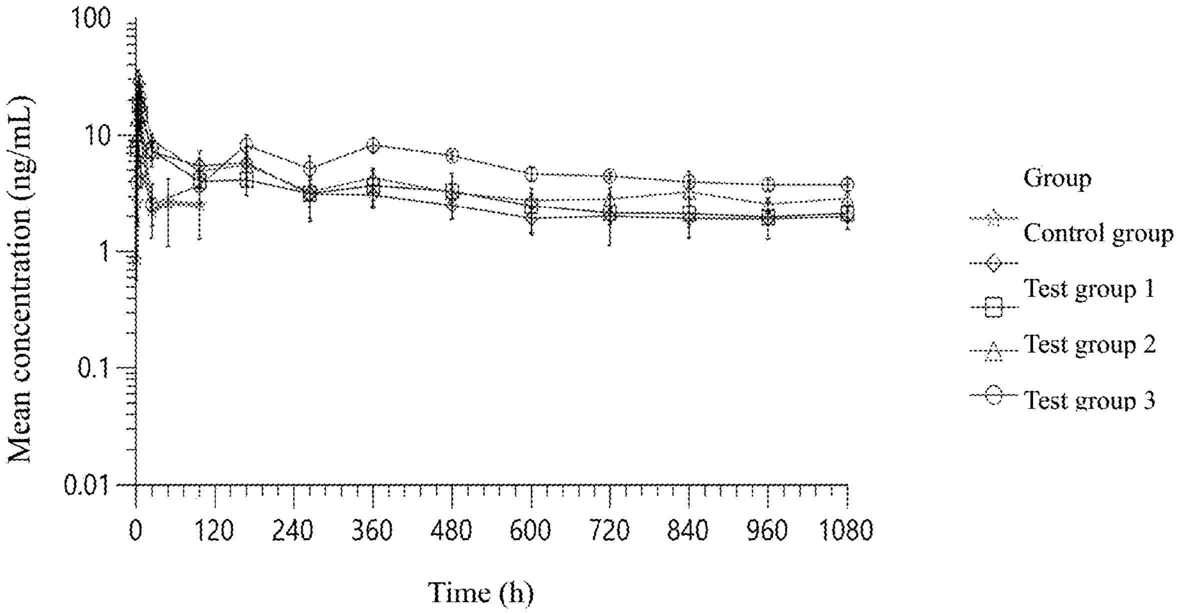
FIG. 14 shows mean drug concentration-time curves in the animals in groups G1-G5 in Example 4 after vilazodone administration.

The morphology and size were observed under a scanning electron microscope (FEI, model F50). The voltage of the scanning electron microscope was 10 kv. A beam 2.0 test was run. The electron micrograph of the solid particles of vilazodone in the ground suspension of formula 6 is shown in FIG. 8. Irregular blocky particles of 0.1-0.5 μm are observed.

TABLE 5

The particle size distribution of vilazodone in the compositions of formulas 3, 4 and 5 of Example 3

| Formula No. | D10 (μm) | D50 (μm) | D90 (μm) |
|---|---|---|---|
| 3 | 4.813 | 25.913 | 70.580 |
| 4 | 5.522 | 13.825 | 24.728 |
| 5 | 0.808 | 1.210 | 1.744 |

TABLE 6

The particle size distribution of vilazodone in the suspension of formula 6 of Example 3

| Particle size distribution | Mean (nm) | Standard deviation (nm) | Polydispersity index (PI) | D10 (nm) | D25 (nm) | D50 (nm) | D75 (nm) | D90 (nm) |
|---|---|---|---|---|---|---|---|---|
| Gaussian distribution luminous intensity weight | 304.47 | 108.64 | 0.127 | 180.74 | 224.74 | 285.53 | 363.21 | 451.04 |
| Gaussian distribution volume weight | 316.07 | 112.78 | 0.127 | 187.63 | 233.01 | 296.41 | 377.05 | 468.23 |
| Gaussian distribution quantity weight | 173.63 | 61.96 | 0.127 | 103.07 | 128.00 | 162.83 | 207.13 | 257.21 |

Affecting factor experiments (4500 LUX lighting and 0, 5 and 10 days of standing at the high temperature of 60° C.) were performed, and the related substances in the formulas were measured by HPLC. The results are shown in Table 7. In formulas 3, 4, 5 and 6, the levels of the related substances RRT0.46 (oxidative degradation impurity), RRT1.35 (acid-base degradation impurity), maximum unknown single impurities and total impurities on day 0 were all relatively low; under high-temperature and illumination conditions, neither the known single impurities nor the maximum unknown single impurities increased, and it was only the total impurities that slightly increased. This indicates good stability in the product.

TABLE 7

The related substance content results (%) of the stability tests of the compositions of formulas 3, 4, 5 and 6 of Example 3

| | | High temperature of 60° C. | | | | Illumination | | | |
|---|---|---|---|---|---|---|---|---|---|
| Formula No. | Time | RRT 0.46 | RRT 1.35 | Maximum unknown | Total impurities | RRT 0.46 | RRT 1.35 | Maximum unknown | Total impurities |
| 3 | 0 day | ND | 0.07 | 0.07 | 0.25 | ND | 0.07 | 0.07 | 0.25 |
| | 5 days | ND | 0.08 | 0.08 | 0.32 | ND | 0.07 | 0.07 | 0.31 |
| | 10 days | ND | 0.05 | 0.05 | 0.38 | ND | 0.05 | 0.07 | 0.39 |
| 4 | 0 day | ND | 0.07 | 0.07 | 0.25 | ND | 0.07 | 0.07 | 0.25 |
| | 5 days | ND | 0.08 | 0.08 | 0.32 | ND | 0.07 | 0.08 | 0.45 |
| | 10 days | ND | 0.05 | 0.05 | 0.37 | ND | 0.06 | 0.09 | 0.62 |
| 5 | 0 day | ND | 0.06 | 0.06 | 0.28 | ND | 0.06 | 0.06 | 0.28 |
| | 5 days | ND | 0.07 | 0.07 | 0.32 | ND | 0.06 | 0.07 | 0.40 |
| | 10 days | ND | 0.05 | 0.05 | 0.34 | ND | 0.06 | 0.09 | 0.62 |
| 6 | 0 day | ND | 0.07 | 0.07 | 0.24 | ND | 0.06 | 0.11 | 0.66 |
| | 5 days | NT | NT | NT | NT | ND | 0.09 | 0.12 | 0.64 |
| | 10 days | ND | 0.05 | 0.05 | 0.37 | ND | 0.06 | 0.11 | 0.66 |

*ND: not detected; NT: not tested

Example 4

15 male rats were selected and randomly divided into 5 groups of 3: a control group (group G1: the formula contained 0.8% vilazodone and a 0.25% aqueous solution of the cellulose HPMC), test group 1 (group G2: formula 3 of Example 3), test group 2 (group G3: formula 4 of Example 3), test group 3 (group G4: formula 5 of Example 3) and test group 4 (group G5: formula 6 of Example 3). The control group was intragastrically dosed at 4 mg/kg. The test groups were administered intramuscular injections at a dose of 120 mg/kg.

Blood samples were collected from the animals in group G1 before the first dose (D1) and 0.5 h, 1 h, 2 h, 3 h, 5 h, 7 h and 24 h after the first dose (D1); blood samples were collected from the animals in groups G2-G5 before administration and 1 h, 3 h, 7 h, 24 h, 96 h, 168 h, 264 h, 360 h, 480 h, 600 h, 720 h, 840 h, 960 h and 1080 h after administration. Sample collection tubes containing EDTA-K2 were placed in an ice bath before blood collection; the collected blood was added to the sample collection tubes, and the tubes were manually inverted at least 5 times and kept in the ice bath; the blood samples were all centrifuged at 2-8° C. at 2000 g for 10 min within 2 h of blood collection. After the centrifugation, the plasma was transferred to new labeled Ep tubes and stored at below −60° C. The concentration of vilazodone in the rat plasma was analyzed by the LC-MS/MS method, whose lower limit of quantification is 0.500 ng/mL. The concentration data were analyzed using the non-compartmental model (NCA) of the pharmacokinetic data analysis software WinNonlin 8.0.0.3176. The main pharmacokinetic parameters of vilazodone in animals are shown in Table 8, and the drug concentration-time curves are shown in FIGS. 9-14. The results show that the T1/2 and MRTlast of the test groups are about 100-150 times longer and about 50-70 times longer, respectively, than those of the control group, which indicates that the test formulations have significant sustained-release effects; the Cmax values of the test groups are 40-120% of that of the control group, which indicates that the test formulations pose no risk of burst release, afford stable plasma concentrations and will not easily cause toxic adverse effects.

In this study, no animals in these groups died or were dying, and no significant abnormal reactions were seen. The animals in groups G2-G5 were euthanized after the last blood sample collection, and no significant abnormal pathological changes were seen in the general observation of the administration sites, which indicates good safety in the test formulations.

Example 5

TABLE 9

The formula for the suspension injection of formula 7 of Example 5

| Component | Ratio (%, W/V) | Ratio (%, W/W) |
|---|---|---|
| Vilazodone hydrochloride | 40 | 36.3 |
| Tween 20 | 1 | 0.91 |
| Disodium hydrogen phosphate | 0.38 | 0.34 |
| Sodium dihydrogen phosphate | 0.08 | 0.07 |
| Mannitol | 2.2 | 2.0 |
| Sodium carboxymethylcellulose | 0.23 | 0.21 |
| Sterile water for injection | q.s. 100 | 60.3 |

According to the formulas shown in Table 9, the raw and auxiliary materials were weighed out and well mixed by stirring to form primary suspensions. The primary suspension was added to a 1.5-fold volume of 0.6 mm zirconium beads. The mixture was placed in a grinding jar and ground for 10 h to obtain the vilazodone pharmaceutical composition of formula 7. The grinding was performed in a ball mill, and the parameter settings of the planetary ball mill were as follows: fixed parameters: the diameter of the revolution plate: about 191 mm, the diameter of the rotation cup: about 71 mm, the height of the rotation cup: about 70 mm, the capacity of the rotation cup: 100 mL, the revolution speed of the revolution plate: 10 r/min, and the rotation speed: 720 r/min.

The particle size of formula 7 and the distribution thereof were measured on a laser particle analyzer using the following parameter settings: dispersion medium: water; refractive index of dispersion medium: 1.333; absorbance of sample material: 0.05; refractive index of sample material: 1.711. The particle size distribution data of the solid particles of vilazodone in the suspension of formula 7 are shown in Table 10. Formula 7 was subjected to an accelerated stability test at 40° C. with RH 75%, and the results of the detection of the related substances are shown in Table 11. The related substances did not change significantly, which indicates good stability in the formula.

TABLE 8

The pharmacokinetic parameters of vilazodone in rats after single intragastric doses of 4 mg/kg and intramuscular injections of 120 mg/kg

| Group | Index | T½ (h) | Tmax (h) | Cmax (ng/mL) | AUClast (h · ng/mL) | AUCinf (h · ng/mL) | Vd/F (L/kg) | Cl/F (L/h/kg | MRTlast (h) |
|---|---|---|---|---|---|---|---|---|---|
| G1 | Mean | 5.96 | 5.00 | 26.43 | 217.14 | 236.62 | 148.31 | 17.28 | 7.27 |
| | SD | 0.56 | 0.00 | 5.71 | 40.46 | 44.83 | 28.17 | 2.95 | 0.09 |
| G2 | Mean | 590.89 | 4.33 | 19.66 | 3445.67 | 5135.25 | 20567.10 | 24.04 | 387.68 |
| | SD | 131.39 | 2.31 | 8.83 | 708.17 | 1014.78 | 6722.17 | 5.14 | 40.53 |
| G3 | Mean | 623.66 | 4.33 | 18.40 | 3468.49 | 5416.93 | 20002.18 | 23.23 | 410.26 |
| | SD | 143.16 | 2.31 | 4.99 | 709.56 | 1337.69 | 446.87 | 6.55 | 65.13 |
| G4 | Mean | 922.59 | 3.00 | 31.45 | 4303.85 | 8107.91 | 20663.23 | 15.42 | 421.02 |
| | SD | 191.14 | 0.00 | 4.54 | 931.51 | 2096.34 | 7627.91 | 3.63 | 13.65 |
| G5 | Mean | 710.14 | 58.00 | 10.42 | 5601.30 | 9425.41 | 13072.53 | 12.73 | 498.29 |
| | SD | 136.74 | 95.26 | 1.25 | 507.77 | 149.63 | 2734.72 | 0.20 | 22.54 |

TABLE 10

The particle size distribution of vilazodone in the suspension of formula 7 of Example 5

| D10 (μm) | D25 (μm) | D50 (μm) | D75 (μm) | D90 (μm) |
|---|---|---|---|---|
| 0.873 | 1.125 | 1.550 | 2.074 | 2.597 |

TABLE 11

The accelerated stability related substance results of formula 7 of Example 5

| | | content (%) | | | |
|---|---|---|---|---|---|
| Condition | Time | RRT0.46 | RRT1.35 | Maximum unknown single impurity | Total impurities |
| 40° C. RH75% | 0 month | 0 | 0.03 | 0.04 | 0.18 |
| | 1 month | 0 | 0.06 | 0.04 | 0.21 |
| | 2 month | 0 | 0.06 | 0.03 | 0.19 |
| | 3 month | 0 | 0.07 | 0.04 | 0.20 |

Example 6

TABLE 12

The formulas for the suspension injections of formulas 8-13 of Example 6

| Component | Percentage (W/V%) |
|---|---|
| Vilazodone hydrochloride | 30 |
| Tween 20 | 1.00 |
| Disodium hydrogen phosphate | 0.38 |
| Sodium dihydrogen phosphate | 0.08 |
| Mannitol | 2.20 |
| Sodium carboxymethylcellulose | 0.23 |
| Sterile water for injection | Qs. 100 |

According to the formulas shown in Table 12, the drug substance of different particle sizes and auxiliary materials were weighed out and well mixed by stirring to form suspensions, and formulas 8-13 were obtained. The particle size and the distribution thereof were measured on a laser particle analyzer using the following parameter settings: dispersion medium: water; refractive index of dispersion medium: 1.333; absorbance of sample material: 0.05; refractive index of sample material: 1.711. The suspensions were tested for syringeability by using a 22 g (0.7 mm outer diameter) needle; the ratios of sedimental volume ($H/H_0$) of the suspensions were determined according to the method in General Chapter 0123 of Chinese Pharmacopoeia, 2020 Edition. The particle size distribution data, syringeability and ratios of sedimental volume of solid particles of vilazodone in the suspensions of formulas 8-13 are shown in Table 13. The results show that formulas 11, 12 and 13 can pass through the needle and have ratios of sedimental volume of greater than 0.8, which indicate good injectability and suspendibility.

TABLE 13

The particle size, syringeability and suspendibility results of the suspension injections of formulas 8-13 of Example 6

| | PSD | | | | Ratio of sedimental |
|---|---|---|---|---|---|
| Formula No. | D10 (μm) | D50 (μm) | D90 (μm) | Syringeability | volume (H/H0) |
| 8 | 4.517 | 46.125 | 220.962 | Did not pass through 22 g | 0.29 |
| 9 | 6.708 | 79.638 | 173.21 | Did not pass through 22 g | 0.30 |
| 10 | 7.483 | 46.221 | 102.81 | Did not pass through 22 g | 0.44 |
| 11 | 4.737 | 17.141 | 72.399 | Passed through 22 g | 0.83 |
| 12 | 4.759 | 17.84 | 57.063 | Passed through 22 g | 0.85 |
| 13 | 2.105 | 9.745 | 39.93 | Passed through 22 g | 0.95 |

Example 7

TABLE 14

The formulas for the suspension injections of formulas 14-23 of Example 7

| | Percentage (W/V %) | | | | | | | | | |
|---|---|---|---|---|---|---|---|---|---|---|
| Component | Formula 14 | Formula 15 | Formula 16 | Formula 17 | Formula 18 | Formula 19 | Formula 20 | Formula 21 | Formula 22 | Formula 23 |
| Vilazodone hydrochloride | 40 | 40 | 40 | 40 | 40 | 40 | 40 | 40 | 30 | 40 |
| Tween 20 | 1.00 | 1.00 | 1.00 | 1.00 | 1.00 | 1.00 | 1.00 | 1.00 | 1.00 | 1.00 |
| PVP K12 | 0.3 | 0.3 | 0.3 | 0 | 0 | 0 | 0 | 0 | 0 | 0 |
| Disodium hydrogen phosphate | 0.33 | 0.33 | 0.33 | 0.34 | 0.34 | 0.34 | 0.33 | 0.33 | 0.39 | 0.38 |
| Sodium dihydrogen phosphate | 0.07 | 0.07 | 0.07 | 0.07 | 0.07 | 0.07 | 0.07 | 0.07 | 0.08 | 0.08 |
| Mannitol | 1.8 | 1.6 | 1.8 | 1.8 | 1.7 | 1.6 | 1.6 | 1.6 | 1.9 | 2.2 |
| Sodium carboxymethyl-cellulose | 0 | 0 | 0.2 | 0.2 | 0 | 0.2 | 0.5 | 1.0 | 0.2 | 0.23 |

TABLE 14-continued

| The formulas for the suspension injections of formulas 14-23 of Example 7 | | | | | | | | | | |
|---|---|---|---|---|---|---|---|---|---|---|
| | Percentage (W/V %) | | | | | | | | | |
| Component | Formula 14 | Formula 15 | Formula 16 | Formula 17 | Formula 18 | Formula 19 | Formula 20 | Formula 21 | Formula 22 | Formula 23 |
| Sterile water for injection | Qs. 100 | Qs. 100 | Qs. 100 | Qs. 100 | Qs. 100 | Qs. 100 | Qs. 100 | Qs. 100 | Qs. 100 | Qs. 100 |

According to the formulas shown in Table 14, the drug substance of the particle sizes (D10=8.4 μm, D50=20.6 μm, D90=43.9 μm) and auxiliary materials were weighed out and well mixed by stirring to form suspensions, and formulas 14-23 were obtained. The suspensions were tested for syringeability by using a 22 g (0.7 mm outer diameter) needle and a 23 g (0.6 mm outer diameter) needle; the ratios of sedimental volume ($H/H_0$) of the suspensions were determined according to the method in General. Chapter 0123 of Chinese Pharmacopoeia, 2020 Edition. The osmotic pressures, syringeability and ratios of sedimental volume of formulas 14-23 are shown in Table 15. The results show that the pH of formulas 14-23 is close to the physiological pH, and the osmotic pressures satisfy the isoosmotic requirements. Moreover, when it comes to syringeability, the formulas can all pass through the 22 g needle, and formula 22 can pass through the 23 g needle; the ratios of sedimental volume of formulas 18, 19, 20 and 21 are greater than 0.8 when the concentration of the suspending agent is within the range of 0-1%. The above data indicate that the formulations have good physical properties, injectability and suspendibility.

TABLE 15

The pH, osmotic pressures, syringeability and suspendibility results of the suspension injections of formulas 14-23 of Example 7

| Formula No. | pH | Osmotic pressure (mOsmol/kg) | Syringeability | Ratio of sedimental volume (H/H0) |
|---|---|---|---|---|
| 14 | 7.4 | 319 | Passed through 22 g | NT |
| 15 | 7.4 | 303 | Passed through 22 g | NT |
| 16 | 7.4 | 303 | Passed through 22 g | NT |
| 17 | 7.4 | 297 | Passed through 22 g | NT |
| 18 | 7.4 | 298 | Passed through 22 g | 0.878 |
| 19 | 7.4 | 296 | Passed through 22 g | 0.915 |
| 20 | 7.4 | 293 | Passed through 22 g | 0.951 |
| 21 | 7.4 | 291 | Passed through 22 g | 0.989 |
| 22 | 7.4 | 290 | Passed through 23 g | NT |
| 23 | 7.5 | 291 | Passed through 22 g | NT |

NT: not tested.

The invention claimed is:

1. A vilazodone pharmaceutical composition, which is a liquid injection, comprising: based on a percentage of a mass of an ingredient in grams to the volume of the liquid injection in milliliters, 1.00-50.00% of solid particles of an active ingredient, greater than 0 and not exceeding 5.00% of a wetting agent, 0-5.00% of a stabilizer, 0-5.00% of an osmotic pressure regulator, greater than 0 and not exceeding 5.00% of a buffer, and a solvent, wherein the active ingredient is selected from vilazodone, vilazodone hydrochloride, a solvate thereof, and mixtures thereof, wherein the solid particles of the active ingredient have the following particle size distribution: a Dv(10) of no more than 20 micrometers, a Dv(50) of no more than 50 micrometers, and a Dv(90) of no more than 100 micrometers;

the wetting agent is a polysorbate;

the stabilizer is one or more selected from polyvinylpyrrolidone, sodium deoxycholate, and sodium carboxymethylcellulose;

the osmotic pressure regulator is mannitol;

the buffer is one or more selected from phosphoric acid and phosphate; and the solvent is water.

2. The vilazodone pharmaceutical composition according to claim 1, having a pH value of 6.5-8.0.

3. The vilazodone pharmaceutical composition according to claim 1, wherein the liquid injection further comprises one or more selected from a suspending agent, a buffer, a surfactant, a polymer, an electrolyte, and a non-electrolyte.

4. The vilazodone pharmaceutical composition according to claim 3, wherein the suspending agent comprises one or more selected from sodium carboxymethylcellulose, polyethylene glycol, and povidone;

and/or, the buffer comprises one or more selected from phosphoric acid, phosphate, citric acid, sodium citrate, hydrochloric acid, sodium hydroxide, tris(hydroxymethyl)aminomethane, sodium hydroxide, hydrochloric acid, and a mixture thereof.

5. The vilazodone pharmaceutical composition according to claim 4, wherein:

the antioxidant comprises one or more selected from citric acid, vitamin C, and vitamin E;

and/or, the metal ion chelating agent comprises ethylenediaminetetraacetic acid;

and/or, the poloxamer comprises one or more selected from poloxamer 188, poloxamer 124 and poloxamer 407;

and/or, the polysorbate comprises one or more selected from polysorbate 80 and polysorbate 20;

and/or, the povidone comprises one or more selected from polyvidone K12, polyvidone K17, PLASDONETM C-12 polyvidone, PLASDONETM C-17 polyvidone, and PLASDONETM C-30 polyvidone;

and/or, the polyethylene glycol includes comprises polyethylene glycol 3350;

and/or, the cross-linked polymer comprises sodium carboxymethylcellulose;

and/or, the phosphate comprises one or more selected from sodium dihydrogen phosphate, disodium hydrogen phosphate, anhydrates or hydrates of sodium dihydrogen phosphate, and anhydrates or hydrates of disodium hydrogen phosphate.

6. A preparation method for the vilazodone pharmaceutical composition according to claim 1, comprising the following steps:

step 1: mixing the solid particles of the active ingredient and auxiliaries comprising the wetting agent, the stabilizer, the osmotic pressure regulator, the buffer, and the solvent to obtain a premix; and step 2: grinding the premix obtained in step 1 together with zirconium beads to obtain the vilazodone pharmaceutical composition.

7. A pharmaceutical formulation comprising the vilazodone pharmaceutical composition according to claim 1, wherein the liquid injection is an aqueous suspension.

8. A method for treating depression, comprising administering the vilazodone pharmaceutical composition according to claim 1 to a patient in need thereof.

9. A method of partially agonizing 5-hydroxytryptamine 1A (5-$HT_{1A}$) and/or selectively inhibiting reuptake of 5-hydroxytryptamine (5-HT), comprising administering the vilazodone pharmaceutical composition according to claim 1 to a patient in need thereof.

10. The vilazodone pharmaceutical composition according to claim 1, wherein: the particle size Dv(10) of the solid particles of the active ingredient is not greater than 10 micrometers; the particle size Dv(50) comprising the solid particles of the active ingredient is not greater than 40 micrometers; the particle size Dv(90) of the solid particles of the active ingredient is not greater than 80 micrometers;

or, the particle size Dv(10) of the solid particles of the active ingredient is not greater than 8 micrometers; the particle size Dv(50) of the active ingredient is not greater than 30 micrometers; the particle size Dv(90) of the solid particles of the active ingredient is not greater than 50 micrometers.

11. The vilazodone pharmaceutical composition according to claim 1, wherein:

the solid particles of the active ingredient is of 5.00-30.00%;

and/or, the wetting is of greater than 0 and not exceeding 2.00%;

and/or, the osmotic pressure regulator is of 1.00%-5.00%;

and/or, the stabilizer is of 0-1.00%;

and/or, the buffer in is of greater than 0 and not exceeding 1.00%;

and/or, the wetting agent is one or more selected from polysorbate 20 and polysorbate 80;

and/or, the buffer is one or more selected from sodium dihydrogen phosphate, disodium hydrogen phosphate, anhydrates or hydrates of sodium dihydrogen phosphate, and anhydrates or hydrates of disodium hydrogen phosphate;

and/or, the polyvinylpyrrolidone is PVP K12.

12. The vilazodone pharmaceutical composition according to claim 1, selected from one of the following formulas:

formula av: 30% vilazodone hydrochloride, 1% polysorbate 20, 2.15% mannitol, 0.08% anhydrous sodium dihydrogen phosphate, and 0.4% anhydrous disodium hydrogen phosphate, with the balance being water;

formula bv: 5% vilazodone hydrochloride, 1% polysorbate 20, 0.3% PVP K12, and 0.3% sodium deoxycholate, with the balance being water;

formula cv: 20% vilazodone hydrochloride, 1% polysorbate 20, 0.3% PVP K12, 0.3% sodium deoxycholate, 0.45% disodium hydrogen phosphate, 0.09% sodium dihydrogen phosphate, 2.5% mannitol, and 0.18% sodium carboxymethylcellulose, with the balance being water;

formula dv: 36.3% vilazodone hydrochloride, 0.91% polysorbate 20, 0.34% disodium hydrogen phosphate, 0.07% sodium dihydrogen phosphate, 2.0% mannitol, and 0.21% sodium carboxymethylcellulose, with the balance being water;

formula ev: 30% vilazodone hydrochloride, 1% polysorbate 20, 0.38% disodium hydrogen phosphate, 0.08% sodium dihydrogen phosphate, 2.20% mannitol, and 0.23% sodium carboxymethylcellulose, with the balance being water;

and formula fv: 30-40% vilazodone hydrochloride, 1% polysorbate 20, 0-0.3% PVP K12, 0.33-0.39% disodium hydrogen phosphate, 0.07-0.08% sodium dihydrogen phosphate, 1.6-2.2% mannitol, and 0-1.0% sodium carboxymethylcellulose, with the balance being water.

* * * * *